(12) United States Patent
Matsumura et al.

(10) Patent No.: US 7,893,296 B2
(45) Date of Patent: Feb. 22, 2011

(54) METHOD FOR PRODUCING AN OPTICALLY ACTIVE β-AMINO ACID

(75) Inventors: Kazuhiko Matsumura, Hiratsuka (JP); Xiaoyong Zhang, Hiratsuka (JP); Takao Saito, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 200 days.

(21) Appl. No.: 11/290,440

(22) Filed: Dec. 1, 2005

(65) Prior Publication Data

US 2006/0122418 A1  Jun. 8, 2006

Related U.S. Application Data

(62) Division of application No. 10/628,394, filed on Jul. 29, 2003, now Pat. No. 7,015,348.

(30) Foreign Application Priority Data

Jul. 30, 2002 (JP) .............................. 2002-222149

(51) Int. Cl.
*C07C 229/00* (2006.01)
(52) U.S. Cl. ...................... 560/155; 562/553
(58) Field of Classification Search ................ 560/155, 560/38, 168; 562/553
See application file for complete search history.

(56) References Cited

U.S. PATENT DOCUMENTS

| | | | |
|---|---|---|---|
| 5,859,249 A | 1/1999 | Seido et al. | 546/235 |
| 6,734,324 B2* | 5/2004 | Glufke et al. | 564/200 |
| 6,784,311 B2* | 8/2004 | Fuchs | 560/155 |
| 6,884,887 B1 | 4/2005 | Riermeier et al. | |
| 6,949,677 B2* | 9/2005 | Glufke et al. | 564/200 |
| 7,015,348 B2* | 3/2006 | Matsumura et al. | 560/155 |
| 7,468,459 B2* | 12/2008 | Xiao et al. | 564/336 |

FOREIGN PATENT DOCUMENTS

| | | |
|---|---|---|
| EP | 02/40491 | 5/2002 |
| JP | 10-231286 | 9/1998 |
| WO | 99/59721 | 11/1999 |

OTHER PUBLICATIONS

Lubell et al., {Enantioselective synthesis of b-amino acids based on BINAP-ruthenium(II) catalyzed hydrogenation, Tetrahedron: Asymmetry (1991), 2(7), 543-54}.*
Hsiao et al., {Highly Efficient Synthesis of b-Amino Acid Derivatives via Asymmetric Hydrogenation of Unprotected Enamines, J. Am. Chem. Soc. 2004, 126, 9918-9919}.*
V. Soloshonok et al., "An Enzymatic Entry to Enantiopure β-Amino Acids", SYNLETT, pp. 339-341, May 1993.
Enantioselective Synthesis of β-Amino Acids, edited by Eusebio Juaristi, Wiley-VCH, New York, pp. (v) to (xviii) and pp. 1-491 (1997).
W. Lubell et al., "Enantioselective Synthesis of β-Amino Acids based on BINAP -Ruthenium(II) Catalyzed Hydrogenation", Tetrahedron: Asymmetry, vol. 2, No. 7, pp. 543-554, pp. 543-554,1991.
K. Achiwa et al., "Catalytic Asymmetric Synthesis of Optically Active β-Amino Acids", Tetrahedron Letters, No. 13, pp. 1119-1120, 1978.
D. Heller et al., "Pressure Dependent Highly Enantioselective Hydrogenation of Unsaturated β-Amino Acid Precursors", J. Org. Chem., vol. 66, No. 20, Oct. 5, 2001, pp. 6816-6817.
Patent Abstracts of Japan, vol. 018, No. 680, Dec. 21, 1994 & JP 06 271520 A, Sep. 27, 1994, abstract.
Berlingozzi et al., 1954, CAS: 49:27881.

* cited by examiner

*Primary Examiner*—Daniel M Sullivan
*Assistant Examiner*—Chukwuma O Nwaonicha
(74) *Attorney, Agent, or Firm*—Sughrue Mion, PLLC

(57) ABSTRACT

Disclosed is a producing method of an optically active β-amino acid useful as intermediate for the production of medicines, agricultural. chemicals and physiologically active substances, by means of a catalytic and asymmetric synthesis method of high performance and a high enantiomeric excess, without requiring additional procedures such as introduction and removal of protecting group and so on. The method includes subjecting an enamine to an asymmetric hydrogenation.

10 Claims, No Drawings

METHOD FOR PRODUCING AN OPTICALLY ACTIVE β-AMINO ACID

This application is a divisional of application Ser. No. 10/628,394 filed Jul. 29, 2003 now U.S. Pat. No. 7,015,348.

BACKGROUND OF THE INVENTION

1. Field of the Invention

The present invention relates to a novel method for producing an optically active β-amino acid very important as intermediate for production of medicines, agricultural chemicals and physiologically active substances, and very useful, for example, as intermediate for the synthesis of antibiotics.

2. Description of the Related Art

Up to now, several methods for preparing optically active β-amino acids have been known; for example, 1) the one in which the corresponding racemic β-amino acid is firstly prepared, followed by optical resolution of the product using an optically active resolution agent or an enzyme, or 2) the one by means of asymmetric synthesis, and so on.

Examples of the method 1) include the technique in which an enzyme is used for optical resolution of the racemate, namely, for example, the one where penicillin acylase is used for hydrolyzing selectively one of the optical isomers of the N-phenylacetyl derivative of a β-amino acid (Synlett, 1993, 339). And, known examples of the method 2) include those techniques described in, for example, "Enantioselective Synthesis of β-Amino Acids", edited by Eusebio Juaristi, Wiley-VCH, New York.

However, a technique using the method 1), in which an optically active resolution agent is used for optical resolution of the racemate, requires more than one mole equivalent of the resolution agent to the β-amino acid to be resolved, and, in addition, troublesome operations such as crystallization, separation, and purification for obtaining an optically active β-amino acid. And, a technique using the method 1), in which an enzyme is used for resolving a racemate, has drawbacks in that the substrate to which the method is applicable and the absolute configuration of the product β-amino acids are restricted to the specific ones, although the technique gives β-amino acids of relatively high optical purities.

The method 2), which adopts the technique of asymmetric synthesis, has the problem to require an expensive optically active compound as the reagent in an amount more than stoichiometric to the racemate to be resolved.

As solutions to these problems, several methods for preparing β-amino acids by the catalytic asymmetric synthesis are known.

Examples of the known catalytic asymmetric synthesis include (1) the asymmetric addition of silyl-enol-ethers to imines by using optically active zirconium Lewis-acid catalysts (Chemistry Today (GENDAI KAGAKU), 2000, 348, 34); (2) the catalytic asymmetric hydrogenation of β-acylamino-α,β-unsaturated esters (WO99/59721, Tetrahedron: Asymmetry 1991, 2, 543, Tetrahedron Lett., 19, 1119 (1978) and J. Am. Chem. Soc., 124, 4952 (2002)).

However, all the catalytic asymmetric syntheses mentioned above require protecting the nitrogen atom in the optically active compound with a substituent or a protecting group which induces appropriate asymmetry, although the amount of the optically active compound required for carrying out the catalytic asymmetric synthesis is small. Furthermore, the products obtained by the catalytic asymmetric syntheses still have the protecting groups on the nitrogen atoms and procedures for deprotection and so on are needed to get the desired optically active β-amino acids. This may cause another problem to deprotect under conditions where only the protecting group is removed.

The catalytic asymmetric hydrogenation of the method (2) mentioned above requires introduction of a protecting group such as an acyl group and so on at the amino group in the starting compound and, furthermore, in the step of introduction of the protecting group such as an acyl group to the starting β-amino-α,β-unsaturated esters, either E- or Z-isomer of the ester has to be produced selectively, or after introducing an acyl group, the β-acylamino-α,β-unsaturated ester obtained has to be purified.

Furthermore, the optically active β-amino acids obtained by the catalytic asymmetric hydrogenation of β-acylamino-α,β-unsaturated esters are still in the form protected at the amino group with, for example, an acyl group. Therefore, the acyl group has to be removed under conditions where, for example, the ester group is not hydrolyzed. These are problems in the known methods.

Thus, developing a generally applicable and highly efficient catalytic method for the production of an optically active β-amino acid, which does not require troublesome procedure such as introduction of a protecting group in the starting compound and deprotection of the protecting group for obtaining the objective optically active β-amino acid, has been eagerly longed for.

JP-A-H10-231286 discloses a method for producing 2-phenyl-2-(2'-piperidinyl)acetic acid ester derivatives by catalytic asymmetric hydrogenation of 2-phenyl-2-(2'-piperidinylidene)acetic acid derivatives having a secondary amino group.

The starting materials, 2-phenyl-2-(2'-piperidinylidene) acetic acid ester derivatives, mentioned above have, however, each a secondary amino group which is also constituting a cyclic structure. No method for obtaining optically active β-amino acids in high optical purities by catalytic asymmetric hydrogenation of β-amino-α,β-unsaturated esters having a primary amino group, namely, an amino group having no substituent on the nitrogen atom, has been known yet.

SUMMARY OF THE INVENTION

The present invention has been worked out through an effort to solve the problems stated above, and provides an efficient method for producing an optically active β-amino acid, useful as intermediary materials for production of medicines, agricultural chemicals and physiologically active substances, by means of a catalytic asymmetric synthesis which does not require additional procedures such as introduction and removal of protecting group and so on, and, therefore, is of high performance and gives a high enantiomeric excess.

The present inventors have made an intensive study on catalytic asymmetric synthesis of optically active β-amino acids and found that the objective β-amino acids can be obtained in a short process and both with high efficiency and enantiomeric excess by subjecting N-unsubstituted enamines to an asymmetric hydrogenation, and completed the present invention.

Namely, the present invention comprises:

1) a method for producing an optically active β-amino acid of formula (2),

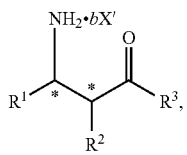

(2)

wherein b is 0 or 1; the symbol * denotes that the carbon atom is a chiral carbon; $R^1$ is a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group or a substituted aryloxy group; $R^2$ is a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxycarbonyl group or an aralkyloxycarbonyl group; $R^3$ is an alkoxy group, a substituted alkoxy group, an aralkyloxy group, a substituted aralkyloxy group, an aryloxy group, a substituted aryloxy group, an amino group or a substituted amino group, X' is an acid, and $R^1$ and $R^2$ or $R^2$ and $R^3$ may be combined together to form a ring provided that $R^1$ and $R^2$ are not a hydrogen atom simultaneously, which comprises subjecting an enamine of formula (1),

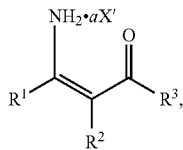

(1)

wherein $R^1$, $R^2$, $R^3$ and X' have the same meanings as described above, and a is 0 or 1, to an asymmetric hydrogenation.

2) the method as described in 1), wherein the asymmetric hydrogenation is carried out in the presence of an acid, 3) the method as described in 1), wherein the asymmetric hydrogenation is carried out in the presence of a fluorine-containing aliphatic alcohol, 4) the method as described in any of 1) to 3), wherein the asymmetric hydrogenation is carried out in the presence of a catalyst for the asymmetric hydrogenation, 5) the method as described in 4), wherein the catalyst for the asymmetric hydrogenation is a transition metal complex, 6) the method as described in 5), wherein the transition metal complex is a complex of a metal which belong to the eighth group of the periodic table, 7) the method as described in 5) or 6), wherein the transition metal complex has a chiral ligand, and 8) the method as described in 7), wherein the chiral ligand is a chiral phosphine ligand.

DETAILED DESCRIPTION OF THE INVENTION

An enamine which can be utilized in the present invention is represented by the following formula (1) (hereinafter, they may be called enamine)

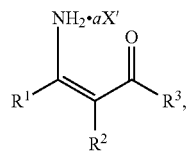

(1)

(wherein, $R^1$, $R^2$, $R^3$, X' and a have the same meanings as stated before).

An optically active β-amino acid which can be obtained by the method of the present invention can be represented by the following formula (2) (hereinafter they may be called as optically active β-amino acid)

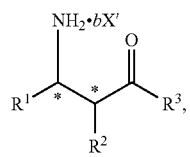

(2)

(wherein, $R^1$, $R^2$, $R^3$, X', b and the symbol * have the same meanings as stated before).

In this connection, in formula (2), when $R^1$ or $R^2$ are hydrogen atoms, the carbon atom to which $R^1$ or $R^2$ bind is not a chiral carbon. $R^1$ and $R^2$ are not a hydrogen atom simultaneously.

What follows is the explanation in detail of the groups represented by $R^1$, $R^2$ and $R^3$, in the formulae (1) and (2).

An alkyl group may be of a straight or a branched one of 1 to 6 carbon atoms. Specific examples of the alkyl group include methyl group, ethyl group, n-propyl group, 2-propyl group, n-butyl, group, 2-butyl group, isobutyl group, tert-butyl group, n-pentyl group, 2-pentyl group, tert-pentyl group, 2-methylbutyl group, 3-methylbutyl group, 2,2-dimethylpropyl group, n-hexyl group, 2-hexyl group, 3-hexyl group, tert-hexyl group, 2-methylpentyl group, 3-methylpentyl group, 4-methylpentyl group and 5-methylpentyl group.

A cycloalkyl group includes, for example, a cycloalkyl group of 3 to 7 carbon atoms, and specific examples of the cycloalkyl group include cyclopropyl group, cyclobutyl group, cyclopentyl group, cyclohexyl group, cycloheptyl group, 2-methylcyclopentyl group, 3-methylcyclopentyl group, cycloheptyl group, 2-methylcyclohexyl group, 3-methylcyclohexyl group and 4-methylcyclohexyl group.

An aralkyl group includes an aralkyl group of 7 to 12 carbon atoms, and specific examples of the aralkyl group include benzyl group, 2-phenylethyl group, 1-phenylpropyl group, 2-phenylpropyl group, 3-phenylpropyl group, 1-phenylbutyl group, 2-phenylbutyl group, 3-phenylbutyl group, 4-phenylbutyl group, 1-phenylpentyl group, 2-phenylpentyl group, 3-phenylpentyl group, 4-phenylpentyl group, 5-phenylpentyl group, 1-phenylhexyl group, 2-phenylhexyl group, 3-phenylhexyl group, 4-phenylhexyl group, 5-phenylhexyl group and 6-phenylhexyl group.

An aryl group includes, for example, an aryl group of 6 to 14 carbon atoms, and specific examples of the aryl group include phenyl group, naphthyl group and anthryl group.

An aliphatic heterocyclic group preferably includes, for example, five- or six-membered aliphatic heterocyclic group which may contain 1 to 3 heteroatoms such as nitrogen atom, oxygen atom and sulfur atom and so on. Specific examples of such aliphatic heterocyclic group include pyrrolidyl-2-on group, piperidino group, piperadinyl group, morpholino group, tetrahydrofuryl group and tetrahydropyranyl group.

An aromatic heterocyclic group preferably include, for example, five- or six-membered, monocyclic or polycyclic aromatic heterocyclic group which contains 1 to 3 heteroatoms such as nitrogen atom, oxygen atom and sulfur atom and so on. Specific examples of the aromatic heterocyclic group include a pyridyl group, an imidazolyl group, a thiazolyl group, a furfuryl group, a pyranyl group, a furyl group a benzofuryl group and a thienyl group.

An alkoxy group includes a straight, a branched or a cyclic one of 1 to 6 carbon atoms. Specific examples of the alkyl group include methoxy group, ethoxy group, n-propoxy group, 2-propoxy group, n-butoxy group, 2-butoxy group, isobutoxy group, tert-butoxy group, n-pentyloxy group, 2-methylbutoxy group, 3-methylbutoxy group, 2,2-dimethylpropyloxy group, n-hexyloxy group, 2-methylpentyloxy group, 3-methylpentyloxy group, 4-methylpentyloxy group, 5-methylpentyloxy group and cyclohexyloxy group.

An aralkyloxy group includes the one of 7 to 12 carbon atoms. Specific examples of the aralkyloxy group include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group and 6-phenylhexyloxy group.

An aryloxy group includes the one of 6 to 14 carbon atoms. Specific examples of the aryloxy group include phenyloxy group, naphthyloxy group and anthryloxy group.

An alkyloxycarbonyl group includes straight and branched ones of 2 to 7 carbon atoms. Specific examples of the alkyloxycarbonyl group include methoxycarbonyl group, ethoxycarbonyl group, propoxycarbonyl group, butoxycarbonyl group, tert-butoxycarbonyl group, pentyloxycarbonyl group, hexyloxycarbonyl group and heptyloxycarbonyl group.

An aralkyloxycarbonyl group includes those of 8 to 12 carbon atoms. Specific examples of the aralkyloxycarbonyl group include benzyloxycarbonyl group and phenylethoxycarbonyl group.

A substituted alkyl group includes an alkyl group in which at least one hydrogen atom is substituted by a group such as an alkyl group, a cycloalkyl group, an alkoxy group, a halogen atom, an amino group, a protected amino group or the like.

A substituted cycloalkyl group includes the cycloalkyl group stated above, in which at least one hydrogen atom in the cycloalkyl group mentioned above is substituted by a group such as an alkyl group, a cycloalkyl group, an alkoxy group, a halogen atom, an amino group, a protected amino group or the like.

A substituted aralkyl group includes the aralkyl group stated above in which at least one hydrogen atom is substituted by a group such as an alkyl group, a cycloalkyl group, a halogenated alkyl group, an alkoxy group, a halogen atom, an alkyl-substituted amino group or the like.

A substituted aryl group includes the aryl group stated above, in which at least one hydrogen atom is substituted by a group such as an alkyl group, a cycloalkyl group, a halogenated alkyl group, an alkoxy group, a halogen atom, an amino group or an alkyl-substituted amino group, or aryl group, in which adjacent two hydrogen atoms on the aryl ring are substituted by a group such as an alkylenedioxy group or the like.

A substituted aliphatic hetecyclic group includes the aliphatic heterocyclic group, in which at least one hydrogen atom is substituted by a group such as an alkyl group, a cycloalkyl group, a halogenated alkyl group, an alkoxy group, a halogen atom or the like.

A substituted aromatic hetecyclic group includes the aromatic heterocyclic group, in which at least one hydrogen atom is substituted by a group such as an alkyl group, a cycloalkyl group, a halogenated alkyl group, an alkoxy group, a halogen atom or the like.

A substituted alkoxy group includes the alkoxy group, in which at least one hydrogen atom is substituted by a group such as an alkyl group, a cycloalkyl group, an alkoxy group, a halogen atom, an amino group, a protected amino group or the like.

A substituted aralkyloxy group includes the aralkyloxy group, in which at least one hydrogen atom is substituted by a group such as an alkyl group, a cycloalkyl group, a halogenated alkyl group, an alkoxy group, a halogen atom, an amino group, an alkyl-substituted amino group or the like.

A substituted aryloxy group includes the aryloxy group stated above, in which at least one hydrogen atom is substituted by a group such as an alkyl group, a cycloalkyl group, a halogenated alkyl group, an alkoxy group, a halogen atom, an amino group, and an alkyl-substituted amino group, or an aryl group, in which adjacent two hydrogen atoms on the aryl ring are substituted by a substituent such as an alkylenedioxy group or the like.

A substituted amino group includes the amino group or the cyclic amino group in which one or two hydrogen atoms of the amino group are substituted by one or two groups such as an alkyl group, a cycloalkyl group, a protecting group or the like.

What follows is the explanation about the substituent group in each of the substituted groups, namely the substituted alkyl, cycloalkyl, aralkyl, aryl, aliphatic heterocyclic, aromatic heterocyclic, alkoxy, aralkyloxy, aryloxy and amino groups.

The terms of the alkyl group, the cycloalkyl group and the alkoxy group have the same meanings as mentioned above.

Halogen atom includes, for example, fluorine atom, chlorine atom, bromine atom and iodine atom.

An alkylenedioxy group may be of 1 to 3 carbon atoms, and the specific examples thereof include methylenedioxy group, ethylenedioxy group, trimethylene dioxy group and propylenedioxy group.

A halogenated alkyl group may be the one formed by halogenation (for example, fluorination, chlorination, bromination and iodination, and so on) of the alkyl group of 1 to 6 carbon atoms mentioned above. The specific examples of such halogenated alkyl group includes chloromethyl group, bromomethyl group, trifluoromethyl group, 2-chloroethyl group, 3-chloropropyl group, 3-bromopropyl group, 3,3,3-trifluoropropyl group.

An alkyl-substituted amino group includes the amino group in which one or two hydrogen atoms of the amino group are substituted by one or two alkyl groups and/or cycloalkyl groups mentioned above. Specific examples of such alkyl-substituted amino group include mono-substituted amino group such as methylamino group, ethylamino group, propylamino group, butylamino group, pentylamino group, hexylamino group and so on, and di-substituted amino group such as dimethylamino group, diethylamino group, dipropylamino group, dibutylamino group, dipentylamino group, dihexylamino group and so on.

As a protecting group, any group which can be used as a protecting group for an amino group is employable. The amino protecting group includes, for example, those described as the amino protecting groups in "PROTECTIVE GROUPS IN ORGANIC SYNTHESIS Second Edition (JOHN WILEY & SONS, INC.)". Specific examples of such amino protecting group include an alkyl group, a cycloalkyl group, an aralkyl group, an acyl group, an alkyloxycarbonyl group and the like.

The terms of an alkyl group, a cycloalkyl group and an aralkyl group have the same meanings as mentioned above. An acyl group may be derived from a carboxylic acid and may be a straight chain, branched or cyclic one of 2 to 7 carbon atoms. Specific examples of the acyl group include acetyl group, propionyl group, butyryl group, pentanoyl group, hexanoyl group and benzoyl group. Examples of alkyloxycarbonyl group include tert-butyloxycarbonyl group, benzyloxycarbonyl group and the like.

An amino group with a protecting group is an amino group protected with the protecting group mentioned above. Specific examples of such amino group bearing protecting group include acetylamino group, benzoylamino group, tert-butyloxycarbonylamino group, benzyloxycarbonylamino group and the like.

As the cyclic amino group, there is exemplified by a cyclic amino group formed by a nitrogen atom and an alkylene chain such as butylene, pentylene or a member selected from a group consisting of —$CH_2CH_2OCH_2CH_2$—, —$CH_2CH_2NHCH_2CH_2$—, —$CH_2CH_2OCO$—, the alkylene chain or the member being attached to the nitrogen atom. The cyclic amino group is concretely exemplified by morpholino group, piperidino group and 1,3-oxazoline-2-on-1-yl.

In cases where $R^1$ and $R^2$ are combined to form a ring, the ring formed may be a monocyclic ring or a polycyclic ring, preferably a five or six membered ring. Also, in cases where $R^2$ and $R^3$ are combined to form a ring, the ring formed may be a monocyclic or polycyclic one, preferably a five or six membered ring.

Examples of the acid represented by X' in the formulae (1) and (2) include an inorganic acid, an organic acids and a Lewis acids.

Examples of the inorganic acid include, for example, hydrochloric acid, hydrobromic acid, sulfuric acid and phosphoric acid, and those of the organic acid include, for example, carboxylic acids such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, glycolic acid and sulfonic acids such as methanesulfonic acid, benzenesulfonic acid, p-toluenesulfonic acid, trifluoromethanesulfonic acid and the like. Each of these acids may be used alone or two or more of them may be used in combination. Among these acids, formic acid, acetic acid, chloroacetic acid and methanesulfonic acid are used more preferably.

In formula (1), a is 0 or 1.

When a=0, the enamine of formula (1) above is represented by formula (3),

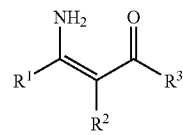

(3)

wherein, $R^1$, $R^2$ and $R^3$ have the same meanings as mentioned above.

When a=1, the enamine of formula (1) above is an acid salt of enamine represented by formula (4),

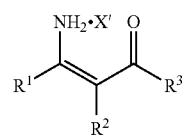

(4)

wherein, $R^1$, $R^2$, $R^3$ and X' have the same meanings as mentioned above.

Among enamines which may be used in the present invention and can be represented by formula (1), β-amino-α,β-unsaturated carboxylic acid derivatives are used preferably. Specific examples of such β-amino-α,β-unsaturated carboxylic acid derivatives include, for example, the compounds as follows:

methyl 3-amino-3-phenylacrylate,
ethyl 3-amino-3-phenylacrylate,
propyl 3-amino-3-phenylacrylate,
isopropyl 3-amino-3-phenylacrylate,
ethyl 3-amino-3-(4-bromophenyl)acrylate,
ethyl 3-amino-3-phenylacrylate methanesulfonate,
methyl 3-amino-3-thiophen-2-yl-acrylate,
methyl 2-amino-1-cyclopentenecarboxylate,
ethyl 2-amino-1-cyclohexenecarboxylate,
ethyl 3-amino-2-methylcrotonate and
ethyl 4-benzyloxy-3-amino-2-butenoate.

As the enamine of formula (1), a commercially available or appropriately prepared enamine can be used.

In formula (2), b is 0 or 1.

When b=0, the optically active β-amino acid of formula (2) above is an optically active β-amino acid of formula (5), wherein $R^1$, $R^2$, $R^3$ and the symbol * have the same meanings as mentioned above.

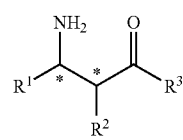

(5)

When b=1, the optically active β-amino acid of formula (2) above is an optically active acid salt of β-amino acid represented by formula (6),

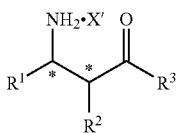

(6)

wherein, $R^1$, $R^2$, $R^3$, $X'$ and the symbol * have the same meanings as mentioned above.

In this connection, in formulae (5) and (6) above, when $R^1$ or $R^2$ are hydrogen atoms, the carbon atom to which $R^1$ or $R^2$ bind is not a chiral carbon. $R^1$ and $R^2$ are not a hydrogen atom simultaneously.

Specific examples of the β-amino acid of formula (2) obtainable by the producing method of the present invention include, for example, those as follows:
methyl (S)-3-amino-3-phenylpropionate,
methyl (R)-3-amino-3-phenylpropionate,
ethyl (S)-3-amino-3-phenylpropionate,
ethyl (R)-3-amino-3-phenylpropionate,
methyl (R)-3-amino-3-phenylpropionate methanesulfonate,
ethyl (S)-3-amino-3-phenylpropionate methanesulfonate,
isopropyl(S)-3-amino-3-phenylpropionate,
isopropyl(R)-3-amino-3-phenylpropionate,
methyl (R)-3-amino-3-thiophen-2-yl-propionate,
methyl (S)-3-aminobutanoate,
methyl (R)-3-aminobutanoate methanesulfonate,
methyl (−)-cis-2-aminocyclopentanecarboxylate and
methyl (−)-cis-2-aminocyclopentanecarboxylate methanesulfonate.

In the producing method of the present invention, the asymmetric hydrogenation of the enamine of formula (1) is carried out in the presence of the catalysts for the asymmetric hydrogenation to give the optically active β-amino acid of formula (2) above with high efficiency and enantiomeric excess.

As the catalyst for the asymmetric hydrogenation, a transition metal complex is preferably used. Among those complexes of the transition metals, the complexes of the VIII group metals of the periodic table are preferable.

Examples of the transition metal complex include, for example, compounds of formula (7) or (8) below, $$M_m L_n X_p Y_q \quad (7)$$

$$[M_m L_n X_p Y_q] Z_s \quad (8)$$

wherein, M is a transition metal of the VIII group, L is a chiral ligand, X is a halogen atom, a carboxylate group, an allyl group, 1,5-cyclooctadiene or norbornadiene, Y is a ligand, Z is an anion, and m, n, p, q, and s mean an integer of 0 to 5.

Examples of the VIII group transition metals of the periodic table represented by M in the formulae (7) and (8) include, same or differently, ruthenium (Ru), rhodium (Rh), iridium (Ir), palladium (Pd) and nickel (Ni).

The chiral ligand represented by L may be, same or differently, monodentate or bidentate ligand. Preferable chiral ligand includes an optically active phosphine ligand, and an optically active bidentate phosphine ligand is more preferable.

Specific examples of the chiral ligand include
cyclohexylanisylmethylphosphine (CAMP),
1,2-bis(anisylphenylphosphino)ethane (DIPAMP),
1,2-bis(alkylmethylphosphino)ethane (BisP*),
2,3-bis(diphenylphosphino)butane (CHIRAPHOS),
1,2-bis(diphenylphosphino)propane (PROPHOS),
2,3-bis(diphenylphosphino)-5-norbornene (NORPHOS),
2,3-O-isopropylidene-2,3-dihydroxy-1,4-bis(diphenylphosphino)butane (DIOP),
1-cyclohexyl-1,2-bis(diphenylphosphino)ethane (CYCPHOS),
1-substituted-3,4-bis(diphenylphosphino)pyrrolidine (DEGPHOS),
2,4-bis(diphenylphosphino)pentane (SKEWPHOS),
1,2-bis(substituted phospholano)benzene (DuPHOS),
1,2-bis(substituted phospholano)ethane (BPE),
1-(substituted phospholano)-2-(diphenylphosphino)benzene (UCAP-Ph),
1-(bis(3,5-dimethylphenyl)phosphino)-2-(substituted phospholano)benzene (UCAP-DM),
1-(substituted phospholano)-2-(bis(3,5-di(t-butyl)-4-methoxyphenyl)phosphino)benzene (UCAP-DTBM),
1-(substituted phospholano)-2-(di-naphthalen-1-yl-phosphino)benzene (UCAP-(1-Nap)),
1-[1',2-bis(diphenylphosphino)ferrocenyl]ethylamine (BPPFA),
1-[1',2-bis(diphenylphosphino)ferrocenyl]ethyl alcohol (BPPFOH),
2,2'-bis(diphenylphosphino)-1,1'-dicyclopentane (BICP),
2,2'-bis(diphenylphosphino)-1,1'-binaphthyl (BINAP),
2,2'-bis(diphenylphosphino)-1,1'-(5,5',6,6',7,7',8,8'-octahydrobinaphthyl) ($H_8$-BINAP),
2,2'-bis(di-p-tolylphosphino)-1,1'-binaphthyl (TOL-BINAP),
2,2'-bis(di(3,5-dimethylphenyl)phosphino)-1,1'-binaphthyl (DM-BINAP),
2,2'-bis(diphenylphosphino)-6,6'-dimethyl-1,1'-biphenyl (BICHEP),
((5,6),(5',6')-bis(methylenedioxy)biphenyl-2,2'-diyl)(bis-diphenylphosphine) (SEGPHOS),
((5,6),(5',6')-bis(methylenedioxy)biphenyl-2,2'-diyl)(bis(3,5-dimethylphenyl)phosphine) (DM-SEGPHOS),
((5,6),(5',6')-bis(methylenedioxy)biphenyl-2,2'-diyl)(bis(3,5-di(tert-butyl)-4-methoxyphenyl)phosphine) (DTBM-SEGPHOS).

The ligands represented by Y are, same or differently, neutral ligands such as aromatic compounds and olefinic compounds and so on. Examples of the aromatic compound include benzene, p-cymene, 1,3,5-trimethylbenzene (mesitylene) and hexamethylbenzene; examples of the olefinic compound include ethylene, 1,5-cyclooctadiene, cyclopentadiene, and norbornadiene; and examples of the other neutral ligand include N,N-dimethylformamide (DMF), acetonitrile, benzonitrile, acetone and chloroform.

Halogen atom represented by X includes chlorine atom, bromine atom and iodine atom.

In formula (8), Z represents an anion. Examples of Z anion includes $BF_4$, $ClO_4$, OTf, $PF_6$, $SbF_6$, $BPh_4$, Cl, Br, I, $I_3$ and sulfonate, wherein, Tf means triflate group ($SO_2CF_3$).

What follows is the detailed explanation about preferable modes of the transition metal complexes mentioned above.

(1) Formula (7), $$M_m L_n X_p Y_q \quad (7)$$

1) When M is Ir or Rh, X is Cl, Br or I, and when L is a monodentate ligand, m=p=2, n=4 and q=0; and when L is a bidentate ligand, m=n=p=2 and q=0.

2) When M is Ru, (i) X is Cl, Br, or I, and Y is a trialkylamino group, and when L is a monodentate ligand, m=2, n=p=4 and q=1; and when L is a bidentate ligand, m=n=2, p=4 and q=1.

(ii) X is Cl, Br or I, and Y is a pyridyl group or a ring-substituted pyridyl group, and when L is a monodentate ligand, m=1, n=p=2 and q=2; and when L is a bidentate ligand, m=n=1, p=2 and q=2, and (iii) X is a carboxylate group, and when L is a monodentate ligand, m=1, n=p=2, and q=0; and when L is a bidentate ligand, m=n=1, p=2, and q=0, and (iv) X is Cl, Br or I, and when L is a monodentate ligand, m=p=2, n=4 and q=0; and when L is a bidentate ligand, m=n=p=2 and q=0.

3) When M is Pd, (i) X is Cl, or I, and when L is a monodentate ligand, m=1, n=2, p=2 and q=0; and when L is a bidentate ligand, m=n=1, p=2 and q=0.

(ii) X is an allyl group, and when L is a monodentate ligand, m=p=2, n=4 and q=0; and when L is a bidentate ligand, m=n=p=2 and q=0.

4) When M is Ni, X is Cl, Br or I, and when L is a monodentate ligand, m=1, n=2, p=2 and q=0; and when L is a bidentate ligand, m=n=1, p=2 and q=0.

(2) Formula (8), $$[M_m L_n X_p Y_q]Z_s \qquad (8)$$

1) When M is Ir or Rh, X is 1,5-cyclooctadiene or norbornadiene, Z is $BF_4$, $ClO_4$, OTf, $PF_6$, $SbF_6$ or $BPh_4$, m=n=p=s=1 and q=0, or m=s=1, n=2 and p=q=0.

2) When M is Ru, (i) X is Cl, Br or I, Y is a neutral ligand such as an aromatic compound and an olefinic compound and Z is Cl, Br, I, $I_3$ or sulfonate, and when L is a monodentate ligand, m=p=s=q=1 and n=2; and when L is a bidentate ligand, m=n=p=s=q=1.

(ii) Z is $BF_4$, $ClO_4$, OTf, $PF_6$, $SbF_6$ or $BPh_4$, and when L is a monodentate ligand, m=1, n=2, p=q=0 and s=2; and when L is a bidentate ligand, m=n=1, p=q=0 and s=2.

3) When M is Pd or Ni, (i) Z is $BF_4$, $ClO_4$, OTf, $PF_6$, $SbF_6$ or $BPh_4$ and when L is a monodentate ligand, m=1, n=2, p=q=0, s=2; and when L is a bidentate ligand, m=n=1, p=q=0 and s=2.

These transition metal complex can be produced by using the known methods.

In the formulae of the transition metal complexes below, the meanings of the symbols used are as follows, L: a chiral ligand; cod: 1,5-cyclooctadiene; nbd: norbornadiene; Tf: a triflate group ($SO_2CF_3$); Ph: phenyl group; and Ac: acetyl group. As specific examples of such transition metal complexes, only the transition metal complexes in which bidentate ligands are used as the chiral ligand are shown in order to avoid complication.

Rhodium Complex:

Rhodium complex can be produced according to the method described in "JIKKEN KAGAKU KOZA, 4th Ed., Volume 18, Organic Metal Complexes, pp. 339-344, published by Maruzen, in 1991". More specifically, Rhodium complex can be produced by reacting bis(cycloocta-1,5-diene)rhodium (I) tetrafluoroboric acid with the chiral ligand.

Specific examples of the rhodium complex include, for example, those which follow:

$[Rh(L)Cl]_2$, $[Rh(L)Br]_2$, $[Rh(L)I]_2$, $[Rh(cod)(L)]BF_4$, $[Rh(cod)(L)]ClO_4$, $[Rh(cod)(L)]PF_6$, $[Rh(cod)(L)]BPh_4$, $[Rh(cod)(L)]OTf$, $[Rh(nbd)(L)]BF_4$, $[Rh(nbd)(L)]ClO_4$, $[(Rh(nbd)(L)]PF_6$, $[Rh(nbd)(L)]BPh_4$ and $[Rh(nbd)(L)]OTf$.

Ruthenium Complex:

The ruthenium complex can be obtained according to the method described in the literature (T. Ikariya, Y. Ishii, H. Kawano, T. Arai, M. Saburi, S. Yoshikawa, and S. Akutagawa, J. Chem. Soc., Chem. Commun., 1985, 922) and in other literatures. More specifically, ruthenium complex can be produced by heating $[Ru(cod)Cl_2]n$ and the chiral ligand under reflux in toluene as solvent in the presence of triethylamine.

Ruthenium complex can be produced also according to the method described in the literature (K. Mashima, K. Kusano, T. Ohta, R. Noyori, H. Takaya, J. Chem. Soc., Chem. Commun., 1989, 1208). More specifically, ruthenium complex can be obtained by heating $[Ru(p\text{-cymene})I_2]_2$ and the chiral ligand in methylene chloride and ethanol with stirring. Specific examples of the ruthenium complex include, for example, those which follow:

$Ru(OAc)_2(L)$, $Ru_2Cl_4(L)_2NEt_3$, $[RuCl(benzene)(L)]Cl$, $[RuBr(benzene)(L)]Br$, $[RuI(benzene)(L)]I$, $[RuCl(p\text{-cymene})(L)]Cl$, $[RuBr(p\text{-cymene})(L)]Br$, $[RuI(p\text{-cymene})(L)]I$, $[Ru(L)](BF_4)_2$, $[Ru(L)](ClO_4)_2$, $[Ru(L)](PF_6)_2$, $[Ru(L)](BPh_4)_2$ and $[Ru(L)](OTf)_2$.

Iridium Complexes:

The iridium complex can be obtained according to the method described in the literature (K. Mashima, T. Akutagawa, X. Zhang, T. Taketomi, H. Kumobayashi, S. Akutagawa, J. Organomet. Chem., 1992, 428, 213) and other literatures. More specifically, the iridium complex can be obtained by allowing a chiral ligand and $[Ir(cod)(CH_3CN)_2]BF_4$ to react in tetrahydrofuran with stirring.

Specific examples of the iridium complexes include, for example, those which follow: $[Ir(L)Cl]_2$, $[Ir(L)Br]_2$, $[Ir(L)I]_2$, $[Ir(cod)(L)]BF_4$, $[Ir(cod)(L)]ClO_4$, $[Ir(cod)(L)]PF_6$, $[Ir(cod)(L)]BPh_4$, $[Ir(cod)(L)]OTf$, $[Ir(nbd)(L)]BF_4$, $[Ir(nbd)(L)]ClO_4$, $[Ir(nbd)(L)]PF_6$, $[Ir(nbd)(L)]BPh_4$ and $[Ir(nbd)(L)]OTf$.

Palladium Complexes:

The palladium complex can be obtained according to the method described in the literature (Y. Uozumi and T. Hayashi, J. Am. Chem. Soc., 1991, 9887) and in others. More specifically, they can be obtained by reacting a chiral ligand with π-allylpalladium chloride.

Specific examples of the palladium complex include, for example, those which follow: $PdCl_2(L)$, $(\pi\text{-allyl})Pd(L)$, $[Pd(L)]BF_4$, $[Pd(L)]ClO_4$, $[Pd(L)]PF_6$, $[Pd(L)]BPh_4$ and $[Pd(L)]OTf$.

Nickel Complex:

Nickel complex can be obtained according to the method described in "JIKKEN KAGAKU KOZA, 4th Ed., Volume 18, Organic Metal Complexes, p. 376, published by Maruzen, in 1991" and in other literatures. The nickel complex can also be obtained, according to the method described in the literature (Y. Uozumi and T. Hayashi, J. Am. Chem. Soc., 1991, 113, 9887), by dissolving a chiral ligand and nickel chloride in a mixed solvent of 2-propanol and methanol and heating the resultant solution with stirring.

Specific examples of the nickel complex include, for example, those which follow: $NiCl_2(L)$, $NiBr_2(L)$ and $NiI_2(L)$.

As the transition metal complexes, both commercial ones and those synthesized in-house can be used.

Among the transition metal complexes which can be used in the present invention, those which have chiral ligands are preferably used, and, furthermore, those which have chiral phosphine ligands as the said chiral ligands are used more preferably.

In the producing method of the present invention, the amount used of the catalyst for the asymmetric hydrogenation depends on the enamine of formula (1) above and the reaction vessel used, mode of the reaction and the economy of the production, it is usually appropriate to select from the range of 1/10 to 1/100,000 in mole or preferably from the range of 1/50 to 1/10,000 in mole against the enamine used.

The producing method of the present invention is preferably carried out in the presence of an acid, when the enamine of formula (3) above is used as the starting enamine. Also, when the acid salt of enamine of formula (4) above is used as the starting enamine, the reaction is not necessarily carried out in the presence of an acid, but the acid may be added only when it is desired.

Furthermore, the producing method of the present invention is preferably carried out in the presence of a fluorine-containing aliphatic alcohol, when the enamine of formula (3) above is used as the starting enamine. Moreover, when the acid salt of enamine of formula (4) above is used as the starting enamine, the reaction is not necessarily carried out in the presence of the fluorine-containing aliphatic alcohol, but the fluorine-containing aliphatic alcohol may be added only when it is desired.

The acid suitably used in the method of the present invention includes an inorganic acid, an organic acid and a Lewis acid and so on.

Examples of the inorganic acid include, for example, hydrochloric acid, hydrobromic acid, sulfuric acid and phosphoric acid, and the organic acid include, for example, a carboxylic acid such as formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, glycolic acid and so on, and a sulfonic acid such as methanesulfonic acid, benzenesulfonic acid, p-toluenesulfonic acid, trifluoromethanesulfonic acid and so on. Each of these acids may be used alone, or as a mixture of two or more kinds of them may be used in combination. Among these acids, formic acid, acetic acid, chloroacetic acid and methanesulfonic acid and so on are preferable.

The amount used of the acid is appropriately selected usually from the range of 0.1 to 10 equivalents, or preferably from the range of 0.5 to 3 equivalents to the enamine used.

The fluorine-containing aliphatic alcohols include, for example, a saturated or unsaturated fluorine-containing aliphatic alcohol of 2 to 10 carbon atoms. Specific examples of the fluorine-containing aliphatic alcohol include, for example, 2,2,2-trifluoroethanol,
2,2-difluoroethanol,
3,3,3-trifluoropropanol,
2,2,3,3,3-pentafluoropropanol,
2,2,3,3-tetrafluoropropanol,
hexafluoroisopropanol,
2-methyl-3,3,3-trifluoroethanol,
3,3,4,4,4-pentafluorobutanol,
4,4,5,5,5-pentafluoropentanol,
5,5,6,6,6-pentafluorohexanol,
1,1,1,3,3,3-hexafluoro-2-propanol, and
3,3,4,4,5,5,6,6,6-nonafluorohexanol. Each of these fluorine-containing alcohols may be used alone, or as a mixture of two or more kinds of them may be used in combination. Among these fluorine-containing alcohols, 2,2,2-trifluoroethanol, 2,2-difluoroethanol, 3,3,3-trifluoropropanol, 2,2,3,3,3-pentafluoropropanol, 2,2,3,3-tetrafluoropropanol, hexafluoroisopropanol, 1,1,1,3,3,3-hexafluoro-2-propanol, and so on are preferable.

The amount used of the fluorine-containing aliphatic alcohol is appropriately selected usually from a range of 5 to 50 weight %, or more preferably from a range of 10 to 40 weight % to the enamine.

The producing method of the present invention can be carried out in a solvent when it is needed. The solvent, however, is not necessarily indispensable because the acid and the fluorine-containing aliphatic alcohol may also serve as solvent and the need for the solvent depends on, for example, the kind of those acid and the fluorine-containing aliphatic alcohol used, and so on.

Preferable solvents are those which dissolve the enamine of formula (1) and the catalyst for the asymmetric hydrogenation.

Specific examples of the solvent include, for example, an aromatic hydrocarbon such as benzene, toluene, xylene and so on; an aliphatic hydrocarbon such as pentane, hexane, heptane, octane and so on; a halogenated hydrocarbon such as methylene chloride, chloroform, carbon tetrachloride, dichloroethane and so on; an ether such as diethyl ether, diisopropyl ether, tert-butyl methyl ether, dimethoxyethane, tetrahydrofuran, dioxane, dioxolane and so on; an alcohol such as methanol, ethanol, 2-propanol, n-butanol, tert-butanol, benzylalcohol and so on; a polyalcohol such as ethylene glycol, propylene glycol, 1,2-propane diol, glycerol and so on; an amide such as N,N-dimethylformamide, N,N-dimethylacetamide and so on; acetonitrile, N-methylpyrrolidone, and dimethylsulfoxide. Each of these solvents may be used alone, or as a mixture of two or more kinds of them may be used in combination.

Among these solvents, alcohols such as methanol, ethanol, 2-propanol, n-butanol, tert-butanol, benzylalcohol and so on are preferable.

The amount used of the solvent is determined under consideration of the solubility of the substrate enamine and costs. In the case of an alcohol solvent, the substrate concentration may be from a low concentration of 1% or less to a state of no solvent or near to no solvent, but it is desirable that the reaction is carried out usually at a concentration of 5 to 50% by weight, or preferably at a concentration of 10 to 40% by weight.

Although a hydrogen pressure of even 1 atm is sufficient in the producing method of the present invention, it is selected from economic consideration and so on usually from the range of 1 to 200 atm, or preferably from the range of 2 to 100 atm. Furthermore, it is also possible, from economical consideration, to keep the catalyst in a highly active state under hydrogen pressure of not more than 10 atm.

The reaction temperature is selected usually from a range of 15 to 100° C., or preferably from a range of 20 to 80° C., taking cost efficiency (cost effectiveness) and so on into consideration, although the reaction itself can be carried out at a temperature as low as −30 to 0° C., or at a high temperature of 100 to 250° C.

Although the reaction time varies with (depending on) the reaction conditions such as the kind and amount used of the catalyst for the asymmetric hydrogenation, the kind and concentration of the enamine used, reaction temperature and pressure of hydrogen and so on, the reaction is usually completed in several minutes to several hours, so, the reaction time is appropriately selected usually from a range of 1 minute to 48 hours and preferably from a range of 10 minutes to 24 hours.

The producing method of the present invention can be carried out both in a batch processing or in a continuous operation.

The optically active β-amino acid obtained by the producing method of the present invention is very useful as intermediate for medicines, agricultural chemicals and physiologically active substances, and useful, for example, as intermediate for the synthesis of antibiotics.

The characteristic of the producing method of the optically active β-amino acid of the present invention is that the method does not require protection of the amino group of the enamine used as the starting material. Therefore, the method of the present invention has the effect of making it possible to obtain desired optically active β-amino acid in a short process without undergoing introduction and removal of protecting group.

EXAMPLES

The present invention is illustrated in more detail by referring to the following Examples and Reference Examples. However, the present invention is not restricted in its scope by these Examples.

Apparatuses used in the following Example and Reference Examples for measuring physical constants and so on are as follows:

Nuclear Magnetic Resonance: (1) DRX500 (BRUKER JAPAN CO. LTD.). $^1$H-NMR (500.13 MHz), $^{13}$C-NMR (125.76 MHz). (2) Gemini 2000 (Varian) $^1$H-NMR (200 MHz);

Melting Point: Yanaco MP-500D;

Optical Rotation: Nihon Bunko DIP-4;

Gas Chromatography (GLC): Hewlett Packard 5890-II;

High Performance Liquid Chromatography (HPLC): Shimadzu Seisakusho LC10AT & SPD10A;

Mass Spectrum (MASS): Hitachi M-80B.

Measurement of enantiomeric excess:
Enantiomeric excess was determined, for example, as follows:
Namely, the enamine obtained is acetylated, for example, with acetic anhydride in the presence of basic substance such as triethylamine to give the corresponding acylated (acetylated) compound of formula (9),

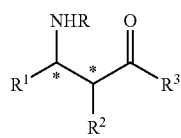
(9)

wherein, R is a protecting group such as an acetyl group and so on, and $R^1$, $R^2$, $R^3$ and the symbol * have the same meanings as mentioned above. The acylated (acetylated) compound thus obtained was then analyzed by means of Gas Chromatography (GLC), using a capillary column CP-Chirasil DEX-CB (0.25 mm I.D.×25 m, 0.25 μm (manufactured by CHROMPACK CO.)).

Reference Example 1

Production of methyl 3-amino-3-phenylacrylate

To a solution of 40.00 g (0.2245 mol) of methyl benzoylacetate in 400 ml of methanol, 70.30 g (1.115 mol) of ammonium formate was added and the mixture was refluxed for 18 hours. After completion of the reaction, the reaction mixture was cooled to room temperature, and the solvent was distilled away under reduced pressure. To the residue, 200 ml of ethyl acetate and 150 ml of water were added, and the mixture was stirred at room temperature for 30 minutes. Then, the organic layer was separated, and the aqueous layer was extracted with 100 ml of ethyl acetate. The organic layer and the extract were combined, washed with water and a brine successively and dried with sodium sulfate. The solvent was removed under reduced pressure, and the residue was then distilled to give the objective methyl 3-amino-3-phenylacrylate (32.44 g, a colorless oil). The yield was 81.6%.

bp: 98-102.5° C./20 Pa; $^1$H-NMR (CDCl$_3$): δ; 3.66 (s, 3H), 4.94 (s, 1H), 7.35-7.40 (m, 3H), 7.49-7.51 (m, 2H); $^{13}$C-NMR (CDCl$_3$): δ: 50.2, 83.9, 126.0, 128.6, 130.1, 137.4, 160.5, 170.6; EI-MS (m/z): 177 ([M]$^+$).

Reference Example 2

Production of ethyl 3-amino-3-phenylacrylate

To a solution of 200.00 g (1.041 mol) of ethyl benzoylacetate in 2,000 ml of methanol, 328.10 g (5.203 mol) of ammonium formate was added, and the resulting mixture was heated under reflux for 14 hours. After completion of the reaction, the reaction mixture was cooled to room temperature, and the solvent was evaporated off under reduced pressure. To the residue, 500 ml of ethyl acetate and 400 ml of water were added, and the mixture was stirred at room temperature for 30 minutes. Then, the organic layer was separated, and the aqueous layer was extracted with 500 ml of ethyl acetate. The organic layers were combined, washed twice with each 400 ml of water and once with 400 ml of a brine successively and dried with sodium sulfate. The solvent was removed under reduced pressure, and the residue was then distilled to give the objective ethyl 3-amino-3-phenylacrylate (190.20 g, a colorless oil). The yield was 95.1%.

bp: 125-130° C./20 Pa; $^1$H-NMR (CDCl$_3$): δ: 1.29 (t, J=7.1 Hz, 3H), 4.17 (q, J=7.1 Hz, 2H), 4.96 (s, 1H), 7.35-7.45 (m, 3H), 7.50-7.55 (m, 2H); $^{13}$C-NMR (CDCl$_3$): δ: 14.5, 58.8, 84.6, 126.1, 128.8, 130.1, 137.6, 160.4, 170.4; EI-MS (m/z): 191 ([M])$^+$).

Reference Example 3

Production of ethyl 3-amino-3-phenylacrylate methanesulfonate

To a solution of 5.00 g (26.01 mmol) of ethyl 3-amino-3-phenylacrylate obtained in Reference Example 2 in 20 ml of toluene, 2.62 g (27.31 mmol) of methanesulfonic acid was added dropwise at room temperature during 30 minutes and then stirred at room temperature for 12 hours. After completion of the reaction, the precipitate was isolated by filtration and washed with 15 ml of toluene and 15 ml hexane successively to give the objective ethyl 3-amino-3-phenylacrylate methanesulfonate (7.29 g, white crystals). The yield was 97.2%.

$^1$H-NMR (DMSO-d$_6$): δ: 1.19 (t, J=7.1 Hz, 3H), 2.49 (s, 3H), 4.05 (q, J=7.1 Hz, 2H), 4.77 (br s, 1H), 7.40-7.50 (m,

3H), 7.58-7.65 (m, 2H), 7.40-8.00 (br, 3H); $^{13}$C-NMR (DMSO-d$_6$): δ: 13.8, 14.4, 57.8, 81.5, 126.2, 128.2, 128.4, 128.6, 130.1, 169.3.

Example 1

Production of methyl (S)-3-amino-3-phenylpropionate

Under a nitrogen atmosphere, 19.2 mg (0.0226 mmol) of Ru(OCOCH$_3$)$_2$((R)-H$_8$-binap), 2.00 g (11.3 mmol) of methyl 3-amino-3-phenylacrylate obtained in Reference Example 1, 1.07 g (11.3 mmol) of chloroacetic acid and 5 ml of methanol were placed in a stainless steel autoclave and the mixture was kept at 50° C. under 3 MPa pressure of hydrogen for 88 hours with stirring. After completion of the reaction, the solvent was distilled off, and the residue was purified by silica gel chromatography (eluent: hexane/ethyl acetate/triethylamine=70/30/0.2) to give the objective methyl (S)-3-amino-3-phenylpropionate (790 mg, colorless oil). The yield was 39.5%.

$^1$H-NMR (CDCl$_3$): δ: 1.75 (s, 2H), 2.64 (dd, J=7.3, 1.0 Hz, 2H), 3.66 (s, 3H), 4.40 (t, J=6.8 Hz, 1H), 7.22-7.25 (m, 1H), 7.30-7.35 (m, 4H); $^{13}$C-NMR (CDCl$_3$): δ: 43.8, 51.4, 52.4, 126.0, 127.2, 128.4, 144.5, 172.2; EI-MS (m/z): 179 ([M]$^+$)

The absolute configuration of the obtained (S)-methyl 3-amino-3-phenylpropionate was determined to be S-form by comparing the measured value of optical rotation $[α]_D^{24}$ −23.7° (c=2.22, CHCl$_3$) of the product above with the value $[α]_D^{26}$ −18.2° (c=1.46, CHCl$_3$) of the authentic 99% ee S isomer in the literature (Bull. Chem. Soc. Jpn. 1998, 71, 1221).

The enantiomeric excess was measured after conversion of the methyl (S)-3-amino-3-phenylpropionate obtained into methyl (S)-3-acetamido-3-phenylpropionate by acetylation with acetic anhydride in the presence of triethylamine, and found to be 94.4% ee.

Example 2

Production of methyl 3-amino-3-phenylpropionate

The reaction was carried out in a manner similar to that in Example 1, except that no chloroacetic acid was added, and the reaction mixture was treated as in Example 1 to give methyl 3-amino-3-phenylpropionate in a yield of 1.2%.

Example 3

Production of methyl (S)-3-amino-3-phenylpropionate

The reaction was carried out in a manner similar to that in Example 1, except that 21.6 mg (0.0226 mmol) of Ru(OCOCH$_3$)$_2$((S)-dm-binap) was used instead of 19.2 mg (0.0226 mmol) of Ru(OCOCH$_3$)$_2$((R)-H$_8$-binap) and that no chloroacetic acid was added. The reaction mixture was treated as in Example 1 to give methyl (S)-3-amino-3-phenylpropionate in a yield of 9.0%.

The enantiomeric excess was determined in the same manner as in Example 1 and found to be 93.4% ee.

Example 4

Production of ethyl (R)-3-amino-3-phenylpropionate

Under a nitrogen atmosphere, 47.7 mg (0.0531 mmol) of Ru(OCOCH$_3$)$_2$((S)-tol-binap), 1.02 g (5.31 mmol) of ethyl 3-amino-3-phenylacrylate produced by Reference Example 2, 5 ml of 2,2,2-trifluoroethanol were placed in a stainless steel autoclave, and the mixture was kept at 50° C. under 3 MPa pressure of hydrogen for 15 hours with stirring. After completion of the reaction, the solvent was distilled off, and the residue was purified by silica gel chromatography (eluent: hexane/ethyl acetate/triethylamine=50/50/5) to give the objective ethyl (R)-3-amino-3-phenylpropionate (0.554 g, pale yellow oil). The yield was 53.8%.

$^1$H-NMR (CDCl$_3$): δ: 1.23 (t, J=7.2 Hz, 3H), 2.04 (br s, 2H), 2.66 (d, J=6.8 Hz, 2H), 4.14 (q, J=7.2 Hz, 2H), 4.42 (t, J=6.8 Hz, 1H), 7.23-7.28 (m, 1H), 7.31-7.39 (m, 4H); $^{13}$C-NMR (CDCl$_3$): δ: 14.1, 44.2, 52.6, 60.5, 126.2, 127.4, 128.6, 144.6, 172.0; EI-MS (m/z): 194 ([M]$^+$)

The absolute configuration of the product was determined to be R-form configuration, due to the fact that the specific optical rotation of the hydrochloride of the ethyl 3-amino-3-phenylpropionate obtained above was found to be $[α]_D^{24}$ −6.21° (c=1.04, CH$_3$OH). The specific optical rotation value of ethyl (R)-3-amino-3-phenylpropionate hydrochloride in the literature is $[α]_D^{22}$ −5.8° (c=1, CH$_3$OH)(J. Med. Chem., 2001, 44, 1158).

The enantiomeric excess was measured after conversion of the ethyl (R)-3-amino-3-phenylpropionate obtained into ethyl (R)-3-acetamido-3-phenylpropionate by acetylation with acetic anhydride in the presence of triethylamine and found to be 96.6% ee.

Example 5

Production of ethyl (R)-3-amino-3-phenylpropionate

The reaction was carried out in a manner similar to that in Example 4, except that 5 ml of 2,2,3,3,3-pentafluoro-1-propanol was used instead of 5 ml of 2,2,2-trifluoroethanol, and the reaction mixture was treated as in Example 4 to give the objective ethyl (R)-3-amino-3-phenylpropionate (0.500 g, pale yellow oil) in a yield of 49.5%.

The enantiomeric excess was determined in a manner similar to that in Example 4 and found to be 95.8% ee.

Example 6

Production of ethyl (R)-3-amino-3-phenylpropionate

Under a nitrogen atmosphere, 31.1 mg (0.0347 mmol) of Ru(OCOCH$_3$)$_2$((S)-tol-binap), 1.00 g (3.47 mmol) of ethyl 3-amino-3-phenylacrylate methanesulfonate obtained in Reference Example 3 and 5 ml of ethanol were placed in a stainless steel autoclave, and the mixture was kept at 50° C. under 3 MPa pressure of hydrogen for 15 hours with stirring. After completion of the reaction, the solvent was distilled off, and the residue was purified by silica gel chromatography (eluent: hexane/ethyl acetate/triethylamine=50/50/5) to give the objective ethyl (R)-3-amino-3-phenylpropionate (0.550 g, pale yellow oil). The yield was 81.6%.

Example 7

Production of ethyl (S)-3-amino-3-phenylpropionate

The reaction was carried out in a manner similar to that in Example 6, except that 28.5 mg (0.0174 mmol) of [{RuCl((R)-segphos)}$_2$(μ-Cl)$_3$][Me$_2$NH$_2$] was used instead of 31.1 mg (0.0347 mmol) of Ru(OCOCH$_3$)$_2$((S)-tol-binap), and the reaction mixture was treated as in Example 6 to give the objective ethyl (S)-3-amino-3-phenylpropionate (0.560 g, pale yellow oil) in a yield of 83.1%.

The enantiomeric excess was measured after conversion of the ethyl (S)-3-amino-3-phenylpropionate obtained into ethyl (S)-3-acetamido-3-phenylpropionate by acetylation with acetic anhydride in the presence of triethylamine, and found to be 70.9% ee.

Example 8

Production of ethyl (S)-3-amino-3-phenylpropionate methanesulfonate

Under a nitrogen atmosphere, 28.5 mg (0.0174 mmol) of [{RuCl((R)-segphos)}$_2$(µ-Cl)$_3$][Me$_2$NH$_2$], 1.00 g (3.47 mmol) of ethyl 3-amino-3-phenylacrylate methanesulfonate obtained in Reference Example 3 and 5 ml of ethanol were placed in a stainless steel autoclave, and the mixture was kept at 50° C. under 3 MPa pressure of hydrogen for 15 hours with stirring. After completion of the reaction, the solvent was distilled off and the residue was triturated with diethyl ether to give the objective ethyl (S)-3-amino-3-phenylpropionate methanesulfonate (0.877 g, pale yellow solid). The yield was 87.1%.

The enantiomeric excess was measured in a manner similar to that in Example 7 and found to be 71.9% ee.

$^1$H-NMR (CD$_3$OD): δ: 1.20 (t, J=7.1 Hz, 3H), 2.69 (s, 3H), 3.01 (dd, J=6.6, 16.8 Hz, 1H), 3.11 (dd, J=7.7, 16.8 Hz, 1H), 4.14 (dq, J=2.1, 7.1 Hz, 2H), 4.72 (br t, J=7.2 Hz, 1H), 7.40-7.50 (m, 5H); $^{13}$C-NMR (CD$_3$OD): δ: 14.3, 39.4, 39.5, 53.1, 62.4, 128.3, 130.4, 130.6, 137.3, 171.2; EI-MS (m/z): 194 ([M]$^+$)

Example 9

Production of methyl (S)-3-aminobutanoate

Under a nitrogen atmosphere, 78.0 mg (0.0869 mmol) of Ru(OCOCH$_3$)$_2$((S)-tol-binap), 1.00 g (8.69 mmol) of methyl 3-aminocrotonate and 5 ml of 2,2,2-trifluoroethanol were placed in a stainless steel autoclave, and the mixture was kept at 50° C. under 3 MPa pressure of hydrogen for 15 hours with stirring. After completion of the reaction, the solvent was distilled off, and the residue was purified by a silica gel chromatography (eluent: ethyl acetate/methanol/triethylamine=95/5/5) to give the objective methyl (S)-3-aminobutanoate (0.149 g, pale yellow oil) in a yield of 14.6%.

The enantiomeric excess was measured after conversion of the methyl (S)-3-aminobutanoate obtained into methyl (S)-3-acetamidobutanoate by acetylation with acetic anhydride in the presence of triethylamine, and was found to be 96.7% ee.

Example 10

Production of methyl (S)-3-aminobutanoate

The reaction was carried out in a manner similar to that in Example 9, except that 35.5 mg (0.0217 mmol) of [{RuCl((S)-segphos)}$_2$(µ-Cl)$_3$][Me$_2$NH$_2$], 0.500 g (4.34 mmol) of methyl 3-aminocrotonate and 2 ml of 2,2,2-trifluoroethanol were used instead of 78.0 mg (0.0869 mmol) of Ru(OCOCH$_3$)$_2$((S)-tol-binap), 1.00 g (8.69 mmol) of methyl 3-aminocrotonate and 5 ml of 2,2,2-trifluoroethanol, respectively, and except that the reaction was carried out 80° C. instead of 50° C. The reaction mixture was treated as in Example 9 to give the objective methyl (S)-3-aminobutanoate (0.433 g, pale yellow oil) in a yield of 85.0%.

The enantiomeric excess was determined after conversion into methyl-(S)-3-acetamidobutanoate in a manner similar to that in Example 9 to be 96.1% ee.

Example 11

Production of methyl (S)-3-aminobutanoate

The reaction was carried out in a manner similar to that in Example 9, except that 62.0 mg (0.0690 mmol) of Ru(OCOCH$_3$)$_2$ ((S)-tol-binap), 0.500 g (4.34 mmol) of methyl 3-aminocrotonate and 1.5 ml of 1,1,1,3,3,3-hexafluoro-2-propanol were used instead of 78.0 mg (0.0869 mmol) of Ru(OCOCH$_3$)$_2$((S)-tol-binap), 1.00 g (8.69 mmol) of methyl 3-aminocrotonate and 5 ml of 2,2,2-trifluoroethanol, respectively, and except that the reaction was carried out 80° C. instead of 50° C. The reaction mixture was treated as in Example 9 to give the objective methyl (S)-3-aminobutanoate (0.308 g, pale yellow oil) in a yield of 60.5%.

The enantiomeric excess was determined after conversion into methyl-(S)-3-acetamidobutanoate in a manner similar to that in Example 9 to be 95.5% ee.

Example 12

Asymmetric Hydrogenation of methyl 3-(n-butylamino)crotonate

The reaction was carried out in a manner similar to that in Example 9, except that 26.2 mg (0.0292 mmol) of Ru(OCOCH$_3$)$_2$((S)-tol-binap), 0.500 mg (2.92 mmol) of methyl 3-(n-butylamino)crotonate and 2.5 ml of 10% hydrogen chloride-methanol solution were used instead of 78.0 mg (0.0869 mmol) of Ru(OCOCH$_3$)$_2$((S)-tol-binap), 1.00 g (8.69 mmol) of methyl 3-aminocrotonate and 5 ml of 2,2,2-trifluoroethanol, respectively, and except that the reaction was carried out for 16 hours instead of 15 hours, and the reaction mixture was treated as in Example 9 to give methyl 3-(n-butylamino)butanoate in a yield of 10.6%.

Example 13

Production of methyl (R)-3-aminobutanoate methanesulfonate

Under a nitrogen atmosphere, 78.0 mg (0.0869 mmol) of Ru(OCOCH$_3$)$_2$((R)-tol-binap), 1.00 g (8.69 mmol) of methyl 3-aminocrotonate, 0.83 g (8.69 mmol) of methanesulfonic acid and 5 ml of methanol were placed in a stainless steel autoclave, and the mixture was kept at 50° C. under 3 MPa pressure of hydrogen for 15 hours with stirring. After completion of the reaction, the solvent was distilled off, and the residue was recrystallized from methanol/ethyl acetate to give the objective methyl (R)-3-aminobutanoate methanesulfonate (1.135 g, white crystals). The yield was 61.3%.

The enantiomeric excess was measured after conversion of the methyl (R)-3-aminobutanoate methanesulfonate obtained into methyl (R)-3-acetamidobutanoate by acetylation with acetic anhydride in the presence of triethylamine, and was found to be 85.0% ee.

$[\alpha]_D^{24}$ −9.3° (c=1.08, CH$_3$OH); $^1$H-NMR (CD$_3$OD): δ: 1.35 (d, J=6.6 Hz), 2.70 (s, 3H), 2.69-2.72 (m, 2H), 3.64-3.72

(m, 1H), 3.74 (s, 3H); $^{13}$C-NMR (CD$_3$OD): δ: 18.7, 38.8, 39.5, 45.7, 52.6, 172.2; EI-MS (m/z): 118 ([M]$^+$).

Reference Example 4

Production of methyl 3-aminocrotonate p-toluenesulfonate

Under a nitrogen atmosphere, in a round bottom flask fitted with a Dean-Stark trap and reflux condenser, 15.70 g (82.52 mmol) of p-toluenesulfonic acid monohydrate in 60 ml of toluene was refluxed for 2 hours, and then the mixture was cooled to room temperature. To a suspension of 10.00 g (86.86 mmol) of methyl 3-aminocrotonate in 70 ml of toluene, the solution of p-toluenesulfonic acid anhydride in toluene obtained described above was added dropwise at 5° C. for 30 minutes, and then the reaction mixture was stirred for an hour at room temperature. After completion of the reaction the precipitate was isolated by filtration and washed with 30 ml of toluene and 30 ml of hexane successively to give the objective methyl 3-aminocrotonate p-toluenesulfonate (23.29 g, white crystals). The yield was 98.2%.
$^1$H-NMR (DMSO-d$_6$): δ: 1.70-2.10 (br, 3H), 2.28 (s, 3H), 3.49 (s, 3H), 4.15-4.40 (br, 1H), 4.80-6.00 (br, 3H), 7.12 (d, J=8.0 Hz, 2H), 7.48 (d, J=8.0 Hz, 2H).

Example 14

Production of methyl (S)-3-aminobutanoate p-toluenesulfonate

Under a nitrogen atmosphere, 14.3 mg (0.00868 mmol) of [{RuCl((S)-segphos)}$_2$(μ-Cl)$_3$][Me$_2$NH$_2$], 1.00 g (3.48 mmol) of methyl 3-aminocrotonate p-toluenesulfonate obtained in Reference Example 4 and 5 ml of methanol were placed in a stainless autoclave, and the mixture was kept at 50° C. under 3 MPa pressure of hydrogen for 14 hours with stirring. After completion of the reaction, the solvent was distilled off, and the residue was recrystallized from methanol/methyl acetate to give the objective methyl (S)-3-aminobutanoate p-toluenesulfonate (0.473 g, white crystals). The yield was 47.0%.
The enantiomeric excess was determined after conversion into methyl-(S)-3-acetamidobutanoate by acetylation with acetic anhydride in a manner similar to that in Example 9 to be 69.3% ee.
$^1$H-NMR (DMSO-d$_6$): δ: 1.19 (d, J=6.6 Hz, 3H), 2.28 (s, 3H), 2.50-2.70 (m, 2H), 3.40-3.60 (m, 1H), 3.63 (s, 3H), 7.12 (d, J=8.0 Hz, 2H), 7.48 (d, J=8.0 Hz, 2H), 7.70-8.00 (br, 3H).

Reference Example 5

Production of methyl 2-amino-1-cyclopentenecarboxylate

To a solution of 10.00 g (70.35 mmol) of methyl cyclopentanone-2-carboxylate in 100 ml of methanol, 22.18 g (351.74 mmol) of ammonium formate was added, and the resulting mixture was heated under reflux for 24 hours. After completion of the reaction, the reaction mixture was cooled to room temperature, and the solvent was distilled off under reduced pressure. To the residue, 50 ml of ethyl acetate and 30 ml of water were added, and the mixture was stirred at room temperature for 30 minutes. Then, the organic layer was separated, and the aqueous layer was extracted with 50 ml of ethyl acetate. The organic layers were combined, washed twice with each 30 ml of water and once with 30 ml of a brine successively and dried over sodium sulfate. The solvent was removed under reduced pressure, and the residue was recrystallized from methanol to give the objective methyl 2-amino-1-cyclopentenecarboxylate (7.34 g, white crystals). The yield was 73.9%.
m.p.: 95-96° C.; $^1$H-NMR (CDCl$_3$): δ: 1.78-1.86 (m, 2H), 2.43-2.55 (m, 4H), 3.69 (s, 3H), 4.10-7.00 (br, 2H); $^{13}$C-NMR (CDCl$_3$): δ: 20.8, 29.4, 35.0, 50.2, 95.1, 162.0, 168.4; EI-MS (m/z): 141 ([M]$^+$).

Example 15

Production of methyl (−)-cis-2-aminocyclopentanecarboxylate methanesulfonate

Under a nitrogen atmosphere, 63.6 mg (0.0708 mmol) of Ru(OCOCH$_3$)$_2$((R)-tol-binap), 1.00 g (7.08 mmol) of methyl 2-amino-1-cyclopentenecarboxylate obtained in Reference Example 5, 0.68 g (7.084 mmol) of methanesulfonic acid and 5 ml of methanol were placed in a stainless steel autoclave, and the mixture was kept at 50° C. under 3 MPa pressure of hydrogen for 15 hours with stirring. After completion of the reaction, the solvent was distilled off and the residue was recrystallized from methanol/ethyl acetate to give the objective methyl (−)-cis-2-aminocyclopentanecarboxylate methanesulfonate (0.643 g, white crystals). The yield was 37.9%.
$[α]_D^{24}$ −27.5° (c=1.06, CH$_3$OH); $^1$H-NMR (CD$_3$OD): δ: 1.66-1.80 (m, 2H), 1.81-1.91 (m, 2H), 2.70 (s, 3H), 2.84-2.92 (m, 1H), 3.74 (s, 3H), 3.83 (br q, J=ca. 7.5 Hz); $^{13}$C-NMR (CD$_3$OD): δ: 24.1, 30.0, 31.9, 39.5, 49.6, 52.8, 55.3, 174.8; EI-MS (m/z): 143 ([M]$^+$).

Reference Example 6

Production of methyl 3-amino-3-thiophen-2-yl-acrylate

To a solution of 17.83 g (0.09679 mol) of methyl 2-(2-thenoyl)acetate in 180 ml of methanol, 36.62 g (0.5807 mol) of ammonium formate was added, and the resulting mixture was heated under reflux for 38 hours. After completion of the reaction, the reaction mixture was cooled to room temperature, and the solvent was evaporated off under reduced pressure. To the residue, 100 ml of ethyl acetate and 100 ml of water were added, and the mixture was stirred at room temperature for 30 minutes. Then, the organic layer was separated, and the aqueous layer was extracted with 50 ml of ethyl acetate. The organic layers were combined, washed with 40 ml of water and with 40 ml of a brine successively and dried over sodium sulfate. The solvent was removed under reduced pressure, and the residue was then distilled to give the objective methyl 3-amino-3-thiophen-2-yl-acrylate (15.80 g, colorless liquid). The yield was 89.1%.
b.p.: 97° C./10 Pa; $^1$H-NMR (CDCl$_3$): δ: 3.69 (s, 3H), 5.11 (s, 1H), 6.50 (br s, 2H), 7.04-7.06 (dd, J=4.9, 3.9 Hz, 1H), 7.34-7.36 (m, 2H); $^{13}$C-NMR (CDCl$_3$): δ: 50.4, 83.8, 125.6, 127.2, 127.7, 139.8, 153.1, 170.4; EI-MS (m/z): 184 ([M+1]$^+$).

Example 16

Production of (1) methyl (R)-3-amino-3-thiophen-2-yl-propionate methanesulfonate and (2) methyl (R)-3-amino-3-thiophen-2-yl-propionate (1) Under a nitrogen atmosphere, 22.5 mg (0.0271 mmol) of Ru(OCOCH$_3$)$_2$((R)-segphos), 1.00 g (5.46 mmol) of methyl 3-amino-3-thiophen-2-yl-acrylate obtained in Reference Example 6, 525 mg (5.46 mmol) of methanesulfonic acid and 5 ml of methanol were placed in a stainless steel autoclave, and the mixture was kept at 80° C. under 3 MPa pressure of hydrogen for 17 hours with stirring. The enantiomeric excess at the time of termination of the reaction was determined by using HPLC column Chiral CD-Ph (4.6 mm I.D.×25 cm, 5 µm, manufactured by Shiseido CO. Ltd.) to be 73.9% ee. The solvent was then distilled off and, to the residue, 15 ml of ethyl acetate was added, and the mixture was stirred at room temperature for 2 hours. Then, the resulting slurry was filtered at room temperature, and the solid obtained was washed twice with 3 ml each of ethyl acetate and dried in vacuo at 50° C. for 18 hours to give methyl (R)-3-amino-3-thiophen-2-yl-propionate methanesulfonate as white solid (993 mg). The ratio of methyl (R)-3-amino-3-thiophen-2-yl-propionate to methanesulfonic acid in the salt obtained was found to be 1:1.9 based on the result of $^1$H-NMR measurement. The enantiomeric excess of the salt obtained was determined to be 74.2% ee by HPLC using Chiral CD-Ph column.

(2) The methyl (R)-3-amino-3-thiophen-2-yl-propionate methanesulfonate obtained in (1) above (801 mg), 5.0 ml of methanol and triethylamine (847 mg, 8.37 mmol) were mixed, and the resulting mixture was stirred at room temperature for 1.5 hours. Then, the solvent was distilled off, and the residue was purified by silica gel chromatography (eluent: hexane/ethyl acetate=70/30) to give methyl (R)-3-amino-3-thiophen-2-yl-propionate (390 mg, a colorless oil). The yield was 47.8%.

[α]$_D^{25}$ 1.1° (c=1.20, CH$_3$OH); $^1$H-NMR (CDCl$_3$): δ: 1.85 (s, 2H), 2.72 (dd, J=16.0, 9.1 Hz, 1H), 2.81 (dd, J=16.0, 4.4 Hz, 1H), 3.70 (s, 3H), 4.70 (dd, J=9.1, 4.4 Hz, 1H), 6.94-6.96 (m, 2H), 7.19-7.21 (m, 1H); $^{13}$C-NMR (CDCl$_3$): δ: 44.3, 48.4, 51.6, 122.8, 123.9, 126.5, 149.1, 171.8; EI-MS (m/z): 185 ([M]$^+$)

The enantiomeric excess was determined to be 74.3% ee based on the results of the measurement of a methanolic solution of methyl (R)-3-amino-3-thiophen-2-yl-propionate by using a HPLC column Chiral CD-Ph. The value was almost the same as that at the end of the hydrogenation (73.9% ee).

Reference Example 7

Production of ethyl 4-benzyloxy-3-amino-2-butenoate

To a solution of 14.48 g (0.6129 mol) of ethyl 4-benzyloxy-3-oxo-butanoate in 145 ml of methanol, 20.54 g (0.3258 mol) of ammonium formate was added, and the resulting mixture was heated under reflux for 16 hours. After completion of the reaction, the reaction mixture was cooled to room temperature and the solvent was evaporated off under reduced pressure. To the reside, 100 ml of ethyl acetate and 100 ml of water were added, and the mixture was stirred at room temperature for 30 minutes. Then, the organic layer was separated and the aqueous layer was extracted with 50 ml of ethyl acetate. The organic layers were combined, washed twice with each 50 ml of a brine and dried over sodium sulfate. The solvent was removed under reduced pressure, and the residue was then distilled to give the objective ethyl 4-benzyloxy-3-amino-2-butenoate (7.61 g, colorless liquid). The yield was 52.8%.

b.p.: 132-135° C./15 Pa; $^1$H-NMR (CDCl$_3$): δ: 1.23 (t, J=7.1 Hz, 3H), 4.04 (s, 2H), 4.13 (q, J=7.1 Hz, 2H), 4.50 (s, 2H), 4.55 (s, 1H), 5.5 (br s, 1H), 7.28-7.38 (m, 5H), 7.7 (br s, 1H); $^{13}$C-NMR (CDCl$_3$): δ: 14.5, 58.6, 69.6, 72.4, 82.1, 127.8, 128.0, 128.5, 137.1, 158.9, 170.0; EI-MS (m/z): 235 ([M]$^+$).

Example 17

Production of methyl (−)-4-benzyloxy-3-amino-butanoate

Under a nitrogen atmosphere, 17.6 mg (0.0212 mmol) of Ru(OCOCH$_3$)$_2$((R)-segphos), 1.00 g (4.25 mmol) of the ethyl 4-benzyloxy-3-amino-2-butenoate obtained in Reference Example 7, 408 mg (4.25 mmol) of methanesulfonic acid and 5 ml of methanol were placed in a stainless steel autoclave, and the mixture was kept at 80° C. under 3 MPa pressure of hydrogen for 25 hours with stirring. After completion of the reaction, the solvent was distilled off, and the residue was purified by silica gel chromatography (eluent: hexane/ethyl acetate/triethylamine=85/15/2) to give the objective methyl (−)-4-benzyloxy-3-aminobutanoate (440 mg, pale yellow oil). The yield was 46.4%.

[α]$_D^{23}$ −4.8° (c=1.13, CH$_3$OH); $^1$H-NMR (CDCl$_3$): δ: 1.85 (br s, 1H), 2.55 (d, J=6.3 Hz, 2H), 3.02 (br s, 1H), 3.47 (dd, J=9.6, 6.0 Hz, 1H), 3.51 (dd, J=9.6, 4.5 Hz, 1H), 3.68 (s, 3H), 4.21-4.26 (m, 1H), 4.58 (s, 2H), 7.26-7.36 (m, 5H); $^{13}$C-NMR (CDCl$_3$): δ: 38.0, 51.7, 67.1, 73.1, 73.3, 127.65, 127.72, 128.4, 137.8, 172.4; EI-MS (m/z): 224 ([M+1]$^+$).

The enantiomeric excess was determined to be 57.7% ee based on the result of the measurement of a methanolic solution of methyl (−)-4-benzyloxy-3-aminobutanoate by HPLC using Chiral CD-Ph-column.

INDUSTRIAL APPLICABILITY

The producing method of the present invention makes it possible to produce the optically active β-amino acid of excellent optical purity both with small amount of catalyst and in a short process without undergoing troublesome procedures of, for example, deprotection and so on. The optically active β-amino acid obtainable by means of the producing method of the present invention is important as intermediary materials for production of medicines, agricultural chemicals and physiologically active substances, and useful, for example, as intermediate for the production of antibiotics. Furthermore, the producing method of the optically active β-amino acid of the present invention is also industrially very useful, because the method has realized excellent catalytic activity and enantio- and/or diastereo-selectivity.

What is claimed is:

1. A method for producing an optically active β-amino acid derivative of formula (2),

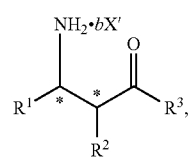

(2)

wherein b is 0 or 1;
the symbol * shows that the carbon atom is a chiral carbon;
$R^1$ is an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group or a substituted aryloxy group;
$R^2$ is a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxycarbonyl group or an aralkyloxycarbonyl group;
$R^3$ is an alkoxy group, a substituted alkoxy group, an aralkyloxy group, a substituted aralkyloxy group, an aryloxy group, a substituted aryloxy group, an amino group or a substituted amino group;
X' is an acid,
provided that at least one of $R^1$ and $R^2$ is an aliphatic heterocyclic group, a substituted aliphatic heterocyclic group, an aromatic heterocyclic group or a substituted aromatic heterocyclic group, except for a thienyl group; or $R^1$ and $R^2$ or $R^2$ and $R^3$ may be combined together to form an aliphatic heterocyclic ring, and wherein when $R^2$ is a hydrogen atom, the carbon atom to which $R^2$ bonds is not a chiral carbon,
which comprises contacting an enamine of formula (1):

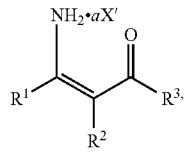

(1)

wherein $R^1$, $R^2$, $R^3$ and X' have the same meanings as described above, and a is 0 or 1,
with hydrogen in the presence of a catalyst for an asymmetric hydrogenation;
wherein, when a is 0, the contacting of the enamine of formula (1) with hydrogen is carried out in the presence of an acid and/or a fluorine-containing aliphatic alcohol.

2. The method as claimed in claim 1, wherein the catalyst for the asymmetric hydrogenation is a transition metal complex.

3. The method as claimed in claim 2, wherein the transition metal complex is a complex of a metal which belong to the VIII group of the periodic table.

4. The method as claimed in claim 2, wherein the transition metal complex has a chiral ligand.

5. The method as claimed in claim 4, wherein the chiral ligand is a chiral phosphine ligand.

6. The method as claimed in claim 1, wherein the contacting of the enamine of formula (1) with hydrogen is carried out in the presence of an acid and a fluorine-containing aliphatic alcohol.

7. The method as claimed in claim 3, wherein the transition metal complex has a chiral ligand.

8. The method as claimed in claim 2, wherein the transition metal complex is represented by formula (7):

$$M_m L_n X_p Y_q$$

wherein, M is a transition metal of the VIII group, L is a chiral ligand, X is a halogen atom, a carboxylate group, an allyl group, 1,5-cyclooctadiene or norbornadiene, Y is a ligand, and m, n, p and q are an integer of 0 to 5.

9. The method as claimed in claim 2, wherein the transition metal complex is represented by formula (8):

$$[M_m L_n X_p Y_q] Z_s$$

wherein, M is a transition metal of the VIII group, L is a chiral ligand, X is a halogen atom, a carboxylate group, an allyl group, 1,5-cyclooctadiene or norbornadiene, Y is a ligand, Z is an anion, and m, n, p, q and s are an integer of 0 to 5.

10. The method as claimed in claim 1, wherein $R^1$ and $R^2$ or $R^2$ and $R^3$ are combined together to form a five- or six-membered aliphatic heterocyclic ring which may contain 1 to 3 heteroatoms.

* * * * *